US009404095B2

(12) United States Patent
Liu et al.

(10) Patent No.: US 9,404,095 B2
(45) Date of Patent: Aug. 2, 2016

(54) ENHANCED HETEROLOGOUS PRODUCTION OF LIPOXYGENASES

(71) Applicant: US NewWin, Inc., Rockville, MD (US)

(72) Inventors: Gaofeng Liu, North Potomac, MD (US); Min-ju Chang, Gaithersburg, MD (US); Averell L. Gnatt, Pikesville, MD (US); Tian Ye, Germantown, MD (US)

(73) Assignee: US NewWin, Inc., Rockville, MD (US)

( * ) Notice: Subject to any disclaimer, the term of this patent is extended or adjusted under 35 U.S.C. 154(b) by 0 days.

(21) Appl. No.: 14/263,105

(22) Filed: Apr. 28, 2014

(65) Prior Publication Data
US 2014/0322388 A1    Oct. 30, 2014

Related U.S. Application Data

(60) Provisional application No. 61/817,077, filed on Apr. 29, 2013.

(51) Int. Cl.
*C12N 9/02* (2006.01)
*A21D 8/04* (2006.01)
*A21D 2/26* (2006.01)

(52) U.S. Cl.
CPC ............. *C12N 9/0069* (2013.01); *A21D 2/267* (2013.01); *A21D 8/042* (2013.01)

(58) Field of Classification Search
None
See application file for complete search history.

(56) References Cited

U.S. PATENT DOCUMENTS

2003/0167544 A1 *  9/2003  Douma et al. ............. 800/320.1

OTHER PUBLICATIONS

NP_001130.1 (last viewed on Jun. 9, 2015).*
Ratelade et al., Production of Recombinant Proteins in the Ion-Deficient BL21(DE3) Strain of *Escherichia coli* in the Absence of the DnaK Chaperone, Appl Environ Microbiol. (2009), vol. 75(11), pp. 3803-3807.*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Branden and Tooze, Introduction to Protein Structure (1999), 2nd edition, Garland Science Publisher, pp. 3-12.*

(Continued)

*Primary Examiner* — Alexander Kim
(74) *Attorney, Agent, or Firm* — Remenick PLLC

(57) ABSTRACT

The invention is directed to the enhanced expression and purification of lipoxygenase enzymes. These enzymes are of wide-spread industrial importance, often produced in heterologous microbial systems. Preferably, the lipoxygenase produced by the methods of the invention is a plant-derived enzyme and expressed at high-levels in a microbial system that includes a protease-deficient host and one or more chaperone expression plasmids. The invention is also directed to amino acid and nucleic acid fragments of the lipoxygenase enzyme including fragments in expression constructs encoding all or a portion of one or more lipoxygenase genes. The invention is also directed to methods of manufacturing bread and other food and also non-food products with lipoxygenase manufactured by the methods of the invention.

24 Claims, 5 Drawing Sheets

(56) References Cited

OTHER PUBLICATIONS

Arolas et al. Expression and purification of integral membrane metallopeptidase HtpX, Protein Expression and Purification (2014), vol. 99, pp. 113-118.*

Weiner et al., (2006), Enzymology and Molecular Biology of Carbonyl Metabolism-12, Purdue University Press, West Lafayette, Indiana, p. 311.*

PCT Search and Patentability Report for PCT/US2014/35657, dated Nov. 18, 2014.

Deb, et al., Cloning, expression, purification, crystallization and preliminary X-ray diffraction studies of a 12R-LOX-chaperone complex. Acta Crystallogr Sect F Struct Biol Cryst Commun. 2011, 67(Pr.8); 903-6; Abstract, p. 904 to p. 905, col. 1; Fig 1, 2 and their legends.

Zhang, et al. Degradation of wood extractives in thermo-mechanical pulp by soybean lipoxygenase. Enzyme and Microbial Technology 2007, 40(4):866-873; Abstract, p. 867, col. 1.

Danielson, Addiction of Soybean Lipoxygenase to All-Purpose Flour and its Effects on Dough Gluten Strength and Bread Quality. Master of Science Thesis. 2007.

* cited by examiner

| Cell Name | Feature of Interest | Genetics | E. Coli K12 or B |
|---|---|---|---|
| BL21(DE3) | DE3 used to express T7 based promoters, protease lon- and ompt- | F- ompT gal dcm lon hsdS$_B$(r$_B$- m$_B$-) λ(DE3 [lacI lacUV5-T7 gene 1 ind1 sam7 nin5]) | B |
| HMS174 | K12 strain, NOT protease deficient, commonly used for protein expression | F- recA1 hsdR(rK12- mK12+) (DE3) (Rif R) | K12 |
| PAM155 | Lon protease deficient | F-, lon-21, galK30, fabA2(ts), rpsL129(strR), thiE1 | K12 |
| PAM153 | Lon protease deficient | F-, lon-21, galK30, λ-?, pyrD36, rpsL129(strR), thiE1 | K12 |
| KD2732 | Lon protease deficient | DM4100: λ-, cysB242(Am), IN(rrnD-rrnE)1 (W3110 derivative), lon-100 | K12 |
| WA834 | OmpT protease deficient | ΔompT504, gal-151, met-100, [malB+]K-12(λS), hsdS10, DE46 | K12 |
| AD202 | OmpT protease deficient | F-, [araD139]B/r, Δ(argF-lac)169, ompT1000::kan, λ-, flhD5301, Δ(fruK-yeiR)725(fruA25), relA1, rpsL150(strR), rbsR22, Δ(fimB-fimE)632(::IS1), deoC1 | K12 |
| JW0554-1 | OmpT protease deficient | F-, Δ(araD-araB)567, ΔlacZ4787(::rrnB-3), ΔompT774::kan, λ-, rph-1, Δ(rhaD-rhaB)568, hsdR514 | K12 |
| SG12079 | Lon/clpP protease deficient | C600*, Δlon-510 ClpP::CM rcsA::Kan | K12 |
| SG12062 | Lon/clpP protease deficient | C600*, ClP::Kan Δlon-510 | K12 |
| ML30010 | Lon/clpP protease deficient | MG1655**, Δlon-510 ClpP::Cat | K12 |
| CAG629 | Lon protease deficient, | F- *lacZ*(am) *pho*(am) *lon supC*(ts) *trp*(am) *rpsL rpoH*(am)*165 zhg::Tn10 mal*(am) | K12 |

**MG1655= F-, lambda-, rph-1. Founder cell line: *C600 = F- tonA21 thi-1 thr-1 leuB6 lacY1 glnV44 rfbC1 fhuA1 λ-

Figure 4

ENHANCED HETEROLOGOUS PRODUCTION OF LIPOXYGENASES

REFERENCE TO RELATED APPLICATIONS

This application claims priority to U.S. Provisional Application No. 61/817,077 of the same title filed Apr. 29, 2013, which is incorporated by reference in its entirety.

SEQUENCE LISTING

The instant application contains a Sequence Listing which has been submitted electronically in ASCII format and is hereby incorporated by reference in its entirety. Said ASCII copy, created on Apr. 28, 2014, is named 3060.002.US_SL.txt and is 29,528 bytes in size.

BACKGROUND

1. Field of the Invention

The invention is directed to systems, compositions and methods for the expression and purification of lipoxygenases, to amino acid and nucleic acid sequences of all or portions of lipoxygenases, to molecular constructs for the expression of lipoxygenases, and, in particular, to methods for the large scale production and use of lipoxygenases in food products.

2. Description of the Background

Lipoxygenases (LOXs; EC1.13.11._), also known as lipoxydases, are non-heme iron-containing dioxygenases distributed in plants and animals. LOXs catalyze hydroperoxidation of polyunsaturated fatty acids in the first step of fatty acid metabolite synthesis, to produce an unsaturated fatty acid hydroperoxide. A LOX definition according to enzyme classification is linoleate: oxygen oxidoreductase (for plant LOX) and arachidonate: oxygen oxidoreductase (for mammalian LOX). In plants, the most common LOX substrates linoleic acid and linolenic acids are converted into a variety of bioactive mediators involved in plant defense, senescence, seed germination, as well as plant growth and development (Grechkin A. Recent developments in biochemistry of the plant lipoxygenase pathway; Prog Lipid Res. 1998 November 37(5):317-52). Lipoxygenases with different specificities, subcellular location, and tissue-specific expression patterns have been identified as ubiquitously found across kingdoms from bacteria to mammals.

LOXs are of commercial value in various industries including but not limited to food-related applications in food processing including bread making (bleaching and improved texture), aroma and flavor enhancement as well as for production of perfumes, paint driers (lipoxygenases: potential starting biocatalysts for the synthesis of signaling compounds. Joo YC, Oh DK. 2012) and pitch control in softwood pulp (Microbial and enzymatic control of pitch in the pulp and paper industry, Ana Gutiérrez & José C. del Río & Angel T. Martínez, Appl Microbiol Biotechnol (2009) 82:1005-4018). Lipoxygenase is present in seeds (e.g. soybeans), grains and many other plant tissues. In the presence of oxygen, lipoxygenase oxidizes unsaturated fatty acids and produces lipid hydroperoxides, which improve dough structure through the oxidation of unsaturated fatty acids and subsequently react with specific chemical components of flour. As a consequence, dough stability and rising is increased, which either or together can increase the volume of the final product.

Regarding the processing of bread, lipoxygenase enzymes offer an advantage over current chemical additives. The flour ingredient industry had long been using chemical bleach, mostly benzoyl peroxide (BPO). Because of potential health concerns over BPO, some Euro countries and China banned the usage of BPO in flour. In the U.S., BPO is still widely used, but the demand keeps shirking although there is currently no safe alternative. Azodiformamide is another chemical alternative, but the dosage is limited to 40 ppm. At this trace dosage, the bleaching effect is quite restrained. In contrast, enzyme additives especially LOXs can replace chemicals to allow for the processing of flour, resulting in the bleaching of bread and its improved texture. In addition, lipid hydroperoxidases decolorize dough and oxidizes carotinoids, converting them into colorless compounds. This blanching of the dough results in lighter colored product, which is highly desired.

With regard to enzymes employed in the food industry, regulations frequently require enzymes to be recognized or proven as safe for use. In the case of lipoxygenases, considering that they are ubiquitously found in plants and consumed by humans and animals alike, plant lipoxygenases are considered safe for use, and therefore, of major value to the industry. Although soy extracts containing high levels of lipoxygenases have been used as an additive for bread manufacturing, soy produces an undesirable taste and smell and, accordingly, not often a useful option.

Because of plant LOX value, many attempts at high-level expression of recombinant plant derived LOX from soy, rice, potato and other sources by heterologous expression in microbial hosts including, but not limited to bacteria such as *E. coli* (BL21 strain), *Bacilli*, and in yeast has been attempted, though production was limited [3-8]. The best of these, although still a poor expression from *E. coli*, was observed at very cold temperatures [8]. Only one lipoxygenase was produced in *Bacilli* at high-levels (~160 mg/L), but the lipoxygenase was from a bacterial enzyme, not a plant and consequently not approved for use in the human food industry [9, 10]. In addition, yields still could not achieve desired levels. Accordingly, a need exists for high level expression of plant lipoxygenases that is generally recognized as safe for use in foods, and easily produced in large quantities.

SUMMARY OF THE INVENTION

The present invention overcomes the problems and disadvantages associated with current strategies and designs, and provides new methods and compositions involving the heterologous expression, purification and use of lipoxygenases.

One embodiment of the invention is directed to the heterologous expression of lipoxygenases in microbes.

Another embodiment of the invention is directed to methods for the purification of lipoxygenases, preferably from heterologous expression systems according to the invention.

Another embodiment of the invention is directed to lipoxygenase polypeptide and nucleic acids sequences and molecular constructs of lipoxygenase coding sequences, preferably for the high level expression of lipoxygenase as compared to expression in wild-type host cells. Preferably wild-type host cells are cells that do not contain a protease deficiency and/or cells that do not contain one or more chaperones.

Another embodiment of the invention is directed to methods for the manufacture of bread products comprising adding lipoxygenases of the invention to a dough containing unsaturated fatty acids and/or carotinoids. Preferably the lipoxygenase reacts with components of the flour forming lipid hydroperoxides increasing the stability of the dough and enhancing the volume of the baked goods.

Another embodiment of the invention is directed to purified lipoxygenase enzyme made by the methods of the invention. When the purified enzyme is added to dough, another embodiment of the invention comprises products made with the purified enzyme added to dough such as, preferably, bread products. The manufacture of bread products of the invention preferably comprises adding lipoxygenases to a dough containing unsaturated fatty acids and/or carotinoids. Preferably the lipoxygenase reacts with components of the flour forming lipid hydroperoxides increasing the stability of the dough and enhancing the volume of the baked goods.

Other embodiments and advantages of the invention are set forth in part in the description, which follows, and in part, may be obvious from this description, or may be learned from the practice of the invention.

DESCRIPTION OF THE FIGURES

FIG. 4 *E. coli* cell lines used to verify experiments.

DESCRIPTION OF THE INVENTION

Figure 1:
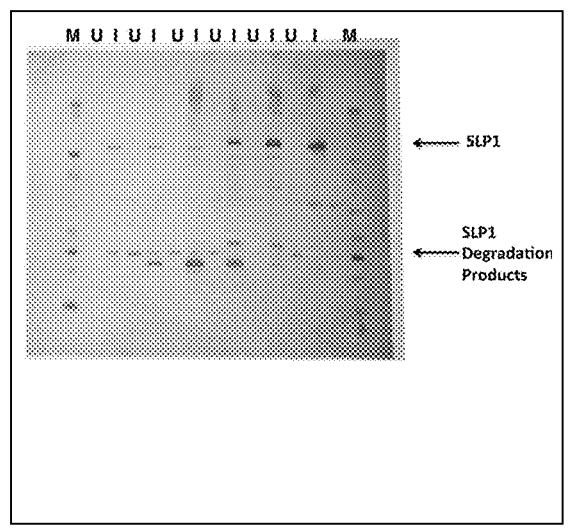
FIG. 1 Western analysis of SLP1 indicates varying profiles of degradation. M=marker. Different K12 cells with different genotypes are presented in sets of "U" (uninduced) and "I" (induced).
Figure 2:
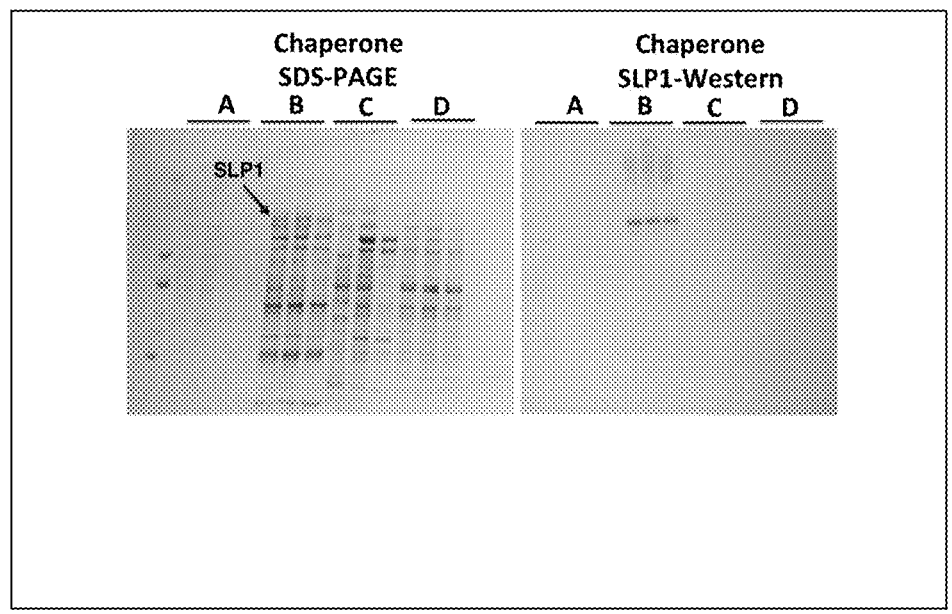
FIG. 2 Co-expression of the GroEL-GroES chaperone enhances SLP1 production. Four chaperones A-D were co-expressed in *E. coli* with SLP1. Left Panel: SLP1 is directed detected as a weak band in SDS-PAGE as a result of Co-expression with Chaperone B. Right Lane: Enhanced expression of SLP1 with co-expressed GroEL-GroES is confirmed by standard Western analysis.
Figure 3:
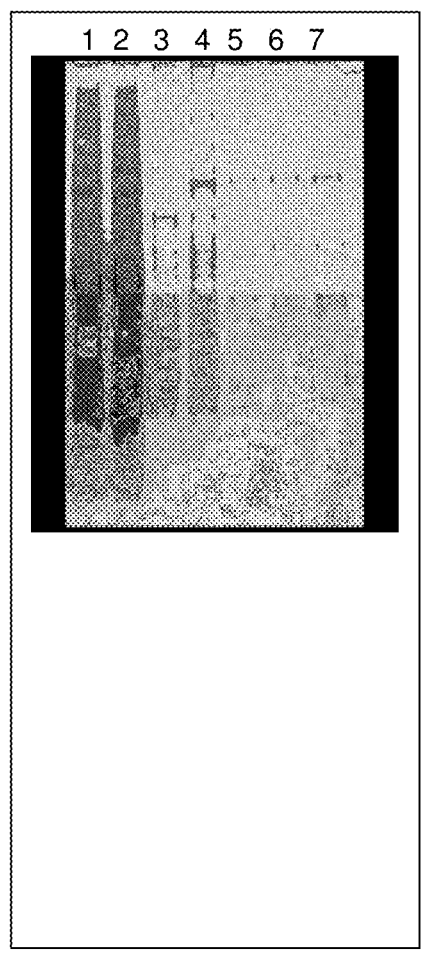
FIG. 3 Single step purification of SLP1 from the 424 vector (native protein sequence, no polyhistidine tag). All lanes: SLP1 lacking a his tag was eluted from Zinc-NTA (IMAC) columns and run in SDS PAGE followed by protein staining: Lanes 1—crude lysate; Lane 2—column flow-through; Lane 3—column wash; Lanes 4-7—Zinc-NTA (IMAC) elution with SLP1 loaded in the presence of 0, 2, 5 and 10 mM imidazole, each eluted with 80 mM imidazole.

Lipoxygenase enzymes (also referred to herein as LOX) are widely used in commercial processing of food products, the manufacture of perfumes and painting products, and in the processing of wood pulp. Although all lipoxygenases catalyze the same basic function, only plant lipoxygenases have been approved by the United States Food and Drug Administration for use in foods and food products. Despite their broad uses, lipoxygenase enzymes are only expressed at low levels and, consequently, commercial quantities are both expensive and difficult to produce.

Despite previous failures in achieving high level LOX expression, it has been surprisingly discovered that considerable enhancement of plant lipoxygenase expression can be achieved. At least part of this high-level of expression is attributed to the selection of sequences being expressed, expression of the sequences in a protease deficient host, and/or the co-expression with one or more chaperone plasmid sequences. Preferable, the increased expression achieved is at a higher level than expression in host cells that do not contain a protease deficiency and/or cells that do not contain one or more chaperone plasmids. Preferably the expression of the one or more proteases is eliminated, reduced to an undetectable level using conventional detection or reduced by at least 90%, all as compared to wild-type expression levels.

One embodiment of the invention comprises a system containing a bacterial cell host, preferably with a deficiency or one or more proteases, containing a coding sequence for lipoxygenase enzyme and preferably a chaperone system comprising one or more chaperone molecules. The system is preferably inducible and also preferably maintained from about 10° C. to about 37° C. for a period of time for maximal expression of enzyme product. The period of time is preferably from minutes to hours to days, and more preferably from about 1 to about 24 hours, more preferably from 2 to 12 hours and more preferably from about 2 to about 4 hours. The cells are preferably maintained at temperatures from about 15° C. to about 25° C. during this period.

The lipoxygenase enzyme may be derived from animal or bacterial cells, and is preferably derived from plant cells. Expression constructs may contain all or a portion of the lipoxygenase gene or coding region. Preferably constructs contain a portion of the coding region sufficient to create functional lipoxygenase activity. Preferably the constructs of the invention encode the sequences of SEQ ID NOs 1-3, or contain the nucleic acid sequences of SEQ ID NOs 4-6. Also preferably the sequence is a functional sequences that generates functional lipoxygenase activity.

Preferably the host cell is a microorganism that rapidly and economically proliferates in vitro such as, for example, one or more of the bacterial cell strains of K12 cells, *E. coli* cells, *Bacillus* cells, *Lactococci* or yeast cells. Also preferably, the host cells contain one or more protease deficiencies as compared to wild-type cells. For *E. coli* host cells, the deficiency is preferably of one or more of the proteases Lon, OMPT, and/or Lon/ClpP.

Preferably the host cells further contain one or more chaperone plasmid expression vectors. Chaperones function in assisting protein folding, benefiting the co-expressed molecules.

Expression of lipoxygenase in the systems of the invention typically involves inducing expression of the lipoxygenase sequence and also preferably the chaperone sequences before, during or after expression of the lipoxygenase, and preferably simultaneously or nearly simultaneously to allow for maximal expression of the enzyme.

Lipoxygenase produced according to methods of the invention can be further isolated and purified. Preferably, purification of lipoxygenase produced according to the methods of the invention involves contact the with immobilized-metal affinity chromatography media. The enzyme remains bound and can be washed with wash buffer and subsequently eluted with elution buffer.

Preferably the increased lipoxygenase expression of the invention is 5 fold greater as compared to expression in wild-type cells (e.g., cells that are not protease deficient and/or cells without one or more expression chaperones), more preferably 10 fold greater, more preferably 50 fold greater, more preferably 100 fold greater, more preferably 200 fold greater, more preferably 300 fold greater, more preferably 400 fold greater, and more preferably 500 fold greater or more.

Lipoxygenase made according to the invention is preferably useful in the manufacture of food products such as bread products (for either, or both bleaching and improving texture), the manufacture of paints thinners, perfumes, aroma and flavor enhancers, as signaling compounds, and for pitch control in softwood pulp in paper industry.

The following examples illustrate embodiments of the invention, but should not be viewed as limiting the scope of the invention.

EXAMPLES

Example 1

LOXs Employed for Protein Production

SLP1 (seed linoleate 13S-lipoxygenase-1 [*Glycine max*] NCBI Reference Sequence: NP_001236153.1, length 839 amino acids) and SLP3 seed linoleate 9S-lipoxygenase-3 [Glycine max] NCBI Reference Sequence: NP_001235383.1) were employed as LOXs for production in microbes. In addition, a shortened version of SLP1 (herein minilox) from amino acid Serine 278 containing an additional methionine before the Serine 278 were cloned and expressed in microbes.

Example 2

Synthesis of DNA Encoding Protein Sequences for SLP1, SLP3 and Minilox Optimized for Expression Optimal gene codon usage in plants and bacteria differ. New DNA encoding sequences for SLP1, SLP3 and minilox were determined and synthetically generated according to instructions (Genscript USA Inc.). The sequence for minilox was identical as that of SLP1 with the exception of having an ATG encoding for an initiator methionine prior to nucleotide bases encoding for SLP1 Serine 278. Optimized sequences with desired cloning sites were created.

Example 3

Cloning of Soybean Lipoxygenase 1 (SLP1) and 3 (SLP3) and MiniLox

Initially, SLP1 and SLP3 were cloned into the pET 47b vector (Novogen) using SmaI-XhoI restriction sites, so that each contained the pET47b initiating methionine and a 6× histidine tag (SEQ ID NO 7). The SLP1 and minilox encoding DNA were then transferred to the DNA2.0 expression vector 424 purple, a low copy number plasmid without the histidine tags using NdeI-XhoI sites, so that expressed proteins would not contain the histidine tags. Similarly, the SLP1 encoding sequence was cloned into the 424-purple vector (herein 424 vector) with the exception of using NdeI-EcoRI cloning sites. The SLP1 encoding sequences were then transferred to the DNA2.0 purple-444 vector (herein 444 vector), a high copy number plasmid using restriction sites NdeI-XhoI. The vectors contained promoters for expression of the insert DNA with the pET47 containing a T7-promotor, and the DNA2.0 vectors contained a T5-promotor.

Example 4

Expression of SLP1, Minilox and SLP3

Vectors were transfected into cell lines. Initially, expression of SLP1 was performed with the 6 histidine (SEQ ID NO 7) tagged SLP1 vector in *E. coli* BL21 cells, an *E. coli* B cell line suitable for the expression of the pET47b vectors. Thereafter, all expression was performed in *E. coli* K12 strains. Expression was tested in LB media, with 50-100 μg/ml ampicillin, and induction of expression for all vectors was with 0.5-1 mM IPTG.

Example 5

Activity Assay

The activity assay utilized linoleic acid as a substrate and colorimetric detection of product. Detected values for the assay varied depending on the substrate preparation, age of substrate, and substrate batch, which may be subject to variation due to oxidation from the environment. As such, approximate expression levels of SLP1 in BL21 are presented as 1 unit/cell OD550 SLP1-LB culture and relative and approximate values for expression in other strains is relative to the BL21 expression. Cell OD550 is defined as a cell density at OD550.

Example 6

Improvement of SLP1 Production

SLP1 expressed with or without a histidine tag using the pET47b vector and BL21 cells was very poor when induced at room temperature. The standard level of activity, 1 unit/OD cells was established for induction at 15° C. with and overnight expression. Dramatically improved activity was observed using the purple-424 vector (herein 424 vector), in the K12 HMS174 cell line (4 units/Cell OD550). Unlike BL21 cells, activity was also observed when induced at 20° C.-25° C. with overnight expression. Slp1 activity could be further enhanced by growing cells at 15° C. for up to several days. In all *E. coli* strains tested, growth at 37 C of was found to generate little or no SLP1 activity, and protein degradation products were observed upon western analysis (FIG. 2).

An additional increase in activity was discovered using protease deficient *E. coli* K12 strains with the 424 vector. Lon, OMPT, or Lon/ClpP mutants all showed a further minimum two-fold increase in activity with (~10 units/cell OD550). The specific *E. coli* cell lines with specific protease deficiencies also showed some similar characteristics of protein degradation (FIG. 3) yet some cell lines had less degradation than others, signifying that proteases play a role in the limited production of lipoxygenases.

An additional enhancement of activity was observed when using the 444 high plasmid copy vector in the K12 Pam155 (lon protease deficient) *E. coli* cell line and with chaperones. Chaperone plasmid sets consisting of five different plasmids from Takara Bio Inc. each designed to express a single or multiple molecular chaperone sets can enable optimal protein expression and folding and reduce protein misfolding. Each Takara plasmid carries an origin of replication (ORF) derived from pACYC and a chloramphenicol-resistance gene ($Cm^r$) gene, which allows the use of *E. coli* expression systems containing ColE1-type plasmids that confer ampicillin resistance. The chaperone genes are situated downstream of the araB or Pzt-1 (tet) promoters and, as a result, expression of target proteins and chaperones can be individually induced if the target gene is placed under the control of different promoters (e.g., lac). These plasmids also contain the necessary regulator (araC or $tet^r$) for each promoter. Takara Bio Inc. plasmids containing chaperones or sets thereof either tetracycline or arabinose inducible were coexpressed with SLP1. These include: groES-groEL, dnaK-dnaJ-grpE, groES-groEL-tig, or tig in plasmids (TakaraBo Inc.). Expression of SLP1 in the presence of groES-groEL alone or with tig (groES-groEL-tig) enhanced the amount of active enzyme produced roughly to 40-60 units/cell OD. Activity was optimal at 15° C. but also observed at or below 25° C. At 37° C., expression was more limited.

Expression of SLP1 in the Pam153 cell with concomitant GroESL chaperone expression, in LB, produces 68 micrograms of SLP1 per milliliter at a bacterial OD550 of 3, when grown in test tubes at 37° C. and induced at 20° C. overnight. However, SLP1 expression in an *E. coli* strain that is not a protease deficient strain and without chaperone expression can either not be detected at all with standard SDS PAGE analysis, or western analysis, or expresses less than 1 μg per milliliter LB under similar conditions at an OD550 of 3 (see FIG. 4). In general, expression of SLP1 in *E. coli* strains grown and induced under optimal conditions was undetectable or less than 1 microgram per milliliter when appropriate chaperones were absent and strains were not protease deficient. However when expressing SLP1 in *E. coli* K12 protease deficient strains with co-expression of an appropriate chaperone, 68 micrograms of SLP1 per milliliter at a bacterial OD550 of 3 was attained.

Example 7

Purification of SPL1

Purification of SLP1 with the 6×his tag (SEQ ID NO 7) was highly effective using standard Ni-NTA IMAC purification. In the 424 or 444 vectors lacking the 6×his tag (SEQ ID NO 7), where SLP1 was encoded by the native SLP1 sequence alone, IMAC was equally efficient though under modified conditions. Nickel and zinc were each tested with similar results and calcium or other divalent metals should do as well. Buffers for IMAC were either 50 mM phosphate or Tris-HCl at pH 7-9, with 400 mM NaCl and 10% glycerol. Cells were disrupted using B-PER (Peirce) or by a homogenizer, in the presence of PMSF as a protease inhibitor. Employing Zinc-NTA, it was discovered that loading the sample in buffer with 10 mM imidazole and elution in buffer with 80 mM imidazole was effective in purification of SLP1. Other column media that effectively binds SLP1 include MonoQ and DEAE, but not negatively charged resins.

Example 8

Novel Information Provides Improved SLP1 Expression

Preliminary studies indicate that relatively poor production of SLP1 is the result of rapid proteolysis accompanied by improper folding of the enzyme. The limited soluble SLP1 and lack of insoluble protein suggests that most of the protein produced was rapidly degraded. Degradation products of SLP1 are visible in different *E. coli* strains with different protease deficient genetic backgrounds (see FIG. 1). An increase in both active enzyme and total protein was observed when inducing at suboptimal growth temperatures, where proteases are less functional. A relative increase in production and activity of SLP1 when protein folding is enhanced by an over-expressed chaperone.

Example 9

High Level Expression of Lipoxygenase in the *E. Coli*, K12

Figure 5:
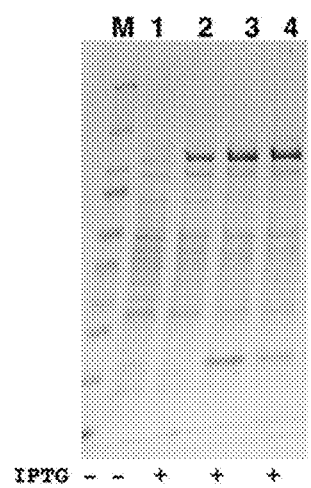
FIG. 5 SLP1 expression in *E. coli*; SDS PAGE protein gel of whole cell K12 *E. coli* lysate expressing SLP1.

Unless otherwise stated, all bacterial media employed in this example was Luria Broth (herein LB, consisting of 10 grams Tryptone, 5 grams Yeast Extract, and 10 grams NaCl, dissolved in 1 liter water, and sterilized for a minimum of 20 minutes in an autoclave). Soybean Lipoxygenase 1 (herein SLP1) was expressed from a plasmid transfected into *E. Coli* K12 cells. FIG. 5 represents an SDS-PAGE protein gel of whole cell soluble proteins extracted from the K12 cells employing the commercial B-PER Protein Extraction Reagent (Pierce, Cat#78243), following company protocols. The highest level of soluble SLP1 protein relative to total soluble protein in the cell extract was 30% or greater and approximated at 34% as estimated by the ImageJ (National Institute of Health public software) analysis software. These levels are consistent with high level production of the enzyme. M=marker, 1 Uninduced, 2 SLP1 induced with 0.5 mM IPTG 3&4 Induced with 0.5 mM IPTG and expressing a molecular chaperone.

CITED REFERENCES

1. Permiakova, M. D. and V. A. Trufanov, Effect of soybean lipoxygenae on baking properties of wheat flour, Prikl Biokhim Mikrobiol, 2011. 47(3): p. 348-54.
2. Permiakova, M. D., et al., [Role of lipoxygenase in the determination of wheat grain quality]. Prikl Biokhim Mikrobiol, 2010. 46(1): p. 96-102.
3. Kanamoto, H., M. Takemura, and K. Ohyama, Cloning and expression of three lipoxygenase genes from liverwort, Marchantia polymorpha L., in *Escherichia coli*. Phytochemistry, 2012. 77: p. 70-8.
4. Osipova, E. V., et al., Recombinant maize 9-lipoxygenase: expression, purification, and properties. Biochemistry Biokhimiia, 2010. 75(7): p. 861-5.
5. Hwang, I. S, and B. K. Hwang, The pepper 9-lipoxygenase gene CaLOX1 functions in defense and cell death responses to microbial pathogens. Plant Physiol, 2010. 152(2): p. 948-67.
6. Padilla, M. N., et al., Functional characterization of two 13-lipoxygenase genes from olive fruit in relation to the biosynthesis of volatile compounds of virgin olive oil. J Agric Food Chem, 2009. 57(19): p. 9097-107.
7. Knust, B. and D. von Wettstein, Expression and secretion of pea-seed lipoxygenase isoenzymes in *Saccharomyces cerevisiae*. Appl Microbiol Biotechnol, 1992. 37(3): p. 342-51.
8. Steczko, J., et al., Effect of ethanol and low-temperature culture on expression of soybean lipoxygenase L-1 in *Escherichia coli*. Protein Expr Purif, 1991. 2(2-3): p. 221-7.

```
Sequence Information
SLP1 polypeptide sequence
                                          (SEQ ID NO 1)
MFSAGHKIKGTVVLMPKNELEVNPDGSAVDNLNAFLGRSVSLQLISATK

ADAHGKGKVGKDTFLEGINTSLPTLGAGESAFNIHFEWDGSMGIPGAFY

IKNYMQVEFFLKSLTLEAISNQGTIRFVCNSWVYNTKLYKSVRIFFANH

TYVPSETPAPLVSYREEELKSLRGNGTGERKEYDRIYDYDVYNDLGNPD

KSEKLARPVLGGSSTFPYPRRGRTGRGPTVTDPNTEKQGEVFYVPRDEN

LGHLKSKDALEIGTKSLSQIVQPAFESAFDLKSTPIEFHSFQDVHDLYE

GGIKLPRDVISTIIPLPVIKELYRTDGQHILKFPQPHVVQVSQSAWMTD

EEFAREMIAGVNPCVIRGLEEFPPKSNLDPAIYGDQSSKITADSLDLDG

YTMDEALGSRRLFMLDYHDIFMPYVRQINQLNSAKTYATRTILFLREDG

TLKPVAIELSLPHSAGDLSAAVSQVVLPAKEGVESTIWLLAKAYVIVND

SCYHQLMSHWLNTHAAMEPFVIATHRHLSVLHPIYKLLTPHYRNNMNIN

ALARQSLINANGIIETTFLPSKYSVEMSSAVYKNWVFTDQALPADLIKR

GVAIKDPSTPHGVRLLIEDYPYAADGLEIWAAIKTWVQEYVPLYYARDD

DVKNDSELQHWWKEAVEKGHGDLKDKPWWPKLQTLEDLVEVCLIIIWIA

SALHAAVNFGQYPYGGLIMNRPTASRRLLPEKGTPEYEEMINNHEKAYL

RTITSKLPTLISLSVIEILSTHASDEVYLGQRDNPHWTSDSKALQAFQK

FGNKLKEIEEKLVRRNNDPSLQGNRLGPVQLPYTLLYPSSEEGLTFRGI

PNSISI
```

SLP3 polypeptide sequence
(SEQ ID NO 2)
MLGGLLHRGHKIKGTVVLMRKNVLDVNSVTSVGGIIGQGLDLVGSTLDT
LTAFLGRSVSLQLISATKADANGKGKLGKATFLEGIITSLPTLGAGQSA
FKINFEWDDGSGIPGAFYIKNFMQTEFFLVSLTLEDIPNHGSIHFVCNS
WIYNAKLFKSDRIFFANQTYLPSETPAPLVKYREEELHNLRGDGTGERK
EWERIYDYDVYNDLGDPDKGENHARPVLGGNDTFPYPRRGRTGRKPTRK
DPNSESRSNDVYLPRDEAFGHLKSSDFLTYGLKSVSQNVLPLLQSAFDL
NFTPREFDSFDEVHGLYSGGIKLPTDIISKISPLPVLKEIFRTDGEQAL
KFPPPKVIQVSKSAWMTDEEFAREMLAGVNPNLIRCLKDFPPRSKLDSQ
VYGDHTSQITKEHLEPNLEGLTVDEAIQNKRLFLLDHHDPIMPYLRRIN
ATSTKAYATRTILFLKNDGTLRPLAIELSLPHPQGDQSGAFSQVFLPAD
EGVESSIWLLAKAYVVVNDSCYHQLVSHWLNTHAVVEPFIIATNRHLSV
VHPIYKLLHPHYRDTMNINGLARLSLVNDGGVIEQTFLWGRYSVEMSAV
VYKDWVFTDQALPADLIKRGMAIEDPSCPHGIRLVIEDYPYTVDGLEIW
DAIKTWVHEYVFLYYKSDDTLREDPELQACWKELVEVGHGDKKNEPWWP
KMQTREELVEACAIIWTASALHAAVNFGQYPYGGLILNRPTLSRRFMP
EKGSAEYEELRKNPQKAYLKTITPKFQTLIDLSVIEILSRHASDEVYLG
ERDNPNWTSDTRALEAFKRFGNKLAQIENKLSERNNDEKLRNRCGPVQM
PYTLLLPSSKEGLTFRGIPNSISI Minilox 1 polypeptide sequence
(SEQ ID NO 3)
MSTPIEFHSFQDVHDLYEGGIKLPRDVISTIIPLPVIKELYRTDGQHI
LKFPQPHVVQVSQSAWMTDEEFAREMIAGVNPCVIRGLEEFPPKSNLD
PAIYGDQSSKITADSLDLDGYTMDEALGSRRLFMLDYHDIFMPYVRQI
NQLNSAKTYATRTILFLREDGTLKPVAIELSLPHSAGDLSAAVSQVVL
PAKEGVESTIWLLAKAYVIVNDSCYHQLMSHWLNTHAAMEPFVIATHR
HLSVLHPIYKLLTPHYRNNMNINALARQSLINANGIIETTFLPSKYSV
EMSSAVYKNWVFTDQALPADLIKRGVAIKDPSTPHGVRLLIEDYPYAA
DGLEIWAAIKTWVQEYVPLYYARDDDVKNDSELQHWWKEAVEKGHGDL
KDKPWWPKLQTLEDLVEVCLIIWIASALHAAVNFGQYPYGGLIMNRP
TASRRLLPEKGTPEYEEMINNHEKAYLRTITSKLPTLISLSVIEILST
HASDEVYLGQRDNPHWTSDSKALQAFQKFGNKLKEIEEKLVRRNNDPS
LQGNRLGPVQLPYTLLYPSSEEGLTFRGIPNSISI SLP1 DNA optimized encoding sequence (with
restriction sites 5'SmaI and 3'XhoI with stop
codon for cloning into pET47b with 6X histidine
tag
(SEQ ID NO 7)) (SEQ ID NO 4)
CCCGGGATGTTTAGTGCTGGTCACAAAATCAAAGGTACCGTGGTCCT
GATGCCGAAAAATGAACTGGAAGTCAACCCGGATGGTAGCGCCGTTG
ATAACCTGAATGCGTTCCTGGGTCGTAGCGTGTCTCTGCAGCTGATT
TCCGCCACCAAAGCAGACGCTCACGGCAAGGGTAAAGTTGGCAAAGA
TACGTTTCTGGAAGGTATTAATACCTCCCTGCCGACCCTGGGTGCCG
GTGAATCAGCTTTCAACATCCATTTCGAATGGGATGGTTCAATGGGC
ATTCCGGGCGCCTTCTACATCAAAAACTACATGCAGGTGGAATTTTT
CCTGAAAAGTCTGACCCTGGAAGCAATCTCCAATCAGGGTACGATTC
GTTTTGTCTGCAACTCGTGGGTGTATAATACCAAACTGTACAAAAGC
GTTCGCATCTTTTTCGCGAACCACACCTATGTTCCGAGCGAAACCCC
GGCACCGCTGGTTTCTTACCGTGAAGAAGAACTGAAAAGTCTGCGCG
GCAATGGTACCGGCGAACGTAAAGAATATGATCGCATTTATGACTAC
GATGTTTACAACGACCTGGGCAATCCGGATAAAGCGAAAAACTGGC
CCGTCCGGTCCTGGGCGGTAGCTCTACCTTCCCGTATCCGCGTCGCG
GTCGTACCGGTCGTGGTCCGACCGTGACCGATCCGAACACCGAAAAA
CAGGGCGAAGTCTTTTATGTGCCGCGCGACGAAAATCTGGGCCATCT
GAAATCTAAAGATGCCCTGGAAATCGGTACCAAAGTCTGTCCCAGA
TTGTGCAACCGGCGTTTGAAAGCGCCTTCGATCTGAAATCTACGCCG
ATTGAATTTCACTCCTTCCAGGACGTTCATGATCTGTATGAAGGCGG
TATCAAACTGCCGCGTGACGTCATTTCAACCATTATCCCGCTGCCGG
TGATCAAAGAACTGTACCGCACGGATGGTCAGCACATTCTGAAATTT
CCGCAACCGCATGTGGTTCAGGTTTCACAATCGGCTGGATGACCGA
TGAAGAATTCGCGCGTGAAATGATCGCCGGCGTTAACCCGTGCGTCA
TTCGCGGTCTGGAAGAATTTCCGCCGAAAAGCAATCTGGACCCCGGCA
ATCTATGGCGATCAGAGTTCCAAAATTACCGCTGACTCTCTGGACCT
GGATGGCTACACGATGGATGAAGCCCTGGGTAGTCGTCGCCTGTTTA
TGCTGGACTATCACGATATCTTCATGCCGTACGTGCGTCAGATTAAC
CAACTGAATTCTGCAAAAACCTATGCTACCCGTACGATCCTGTTTCT
GCGCGAAGACGGCACGCTGAAACCGGTTGCAATTGAACTGAGCCTGC
CGCATTCTGCTGGTGATCTGAGTGCCGCGGTGTCCCAGGTTGTGCTG
CCGGCAAAAGAAGGCGTTGAAAGTACCATCTGGCTGCTGGCGAAAGC
CTATGTTATTGTCAACGATTCATGTTACCATCAACTGATGTCGCACT
GGCTGAATACCCATGCAGCTATGGAACCGTTTGTTATCGCAACGCAT
CGCCACCTGTCTGTCCTGCACCCGATTTATAAACTGCTGACCCCGCA
TTACCGTAACAATATGAACATCAATGCACTGGCTCGCCAGAGTCTGA
TTAACGCGAATGGTATTATCGAAACCACGTTCCTGCCGTCAAAATAT
TCGGTGAAATGTCATCGGCCGTTTACAAAAACTGGGTCTTTACCGA
CCAGGCACTGCCGGCTGATCTGATCAAACGTGGCGTCGCGATTAAAG
ATCCGAGCACCCCGCATGGTGTGCGTCTGCTGATTGAAGACTATCCG
TACGCGGCCGATGGCCTGGAAATCTGGGCAGCTATTAAACCTGGGT
GCAGGAATATGTTCCGCTGTATTACGCACGCGATGACGATGTGAAA
ATGACTCCGAACTGCAACACTGGTGGAAAGAAGCTGTTGAAAAAGGT
CATGGCGACCTGAAAGATAAACCGTGGTGGCCGAAACTGCAGACCCT
GGAAGATCTGGTGGAAGTTTGTCTGATTATCATTTGGATTGCCAGCG
CACTGCATGCCGCGGTGAACTTTGGTCAATATCCGTACGGCGGTCTG
ATTATGAATCGTCCGACCGCAAGCCGTCGCCTGCTGCCGGAAAAAGG -continued

CACGCCGGAATACGAAGAAATGATCAACAACCATGAAAAAGCGTACC

TGCGCACCATCACGAGCAAACTGCCGACCCTGATTAGCCTGTCTGTT

ATCGAAATTCTGTCAACGCACGCGTCGGATGAAGTCTATCTGGGTCA

GCGTGACAACCCGCATTGGACCAGTGATTCCAAAGCGCTGCAGGCCT

TCCAAAAATTCGGCAACAAACTGAAAGAAATCGAAGAAAACTGGTC

CGTCGCAACAATGATCCGAGCCTGCAGGGTAACCGTCTGGGTCCGGT

GCAACTGCCGTATACCCTGCTGTATCCGTCCAGTGAAGAAGGTCTGA

CGTTTCGTGGTATTCCGAACTCCATTTCCATCTGACTCGAG

SLP3 DNA optimized encoding sequence (with restriction sites 5'NdeI and 3'EcoRI and 3'stop codon for cloning into the pJex purple 424 vector from DNA2.0 Inc.

(SEQ ID NO 5)

CATATGCTGGGCGGCCTGCTGCACCGTGGTCATAAAATCAAGGGCA

CCGTGGTCCTGATGCGTAAGAACGTCCTGGATGTGAATAGCGTGAC

CTCGGTCGGCGGTATTATCGGCCAGGGTCTGGACCTGGTGGGTAGC

ACGCTGGATACCCTGACGGCCTTTCTGGGCCGCTCAGTGTCGCTGC

AACTGATCAGCGCAACCAAAGCAGATGCTAACGGCAAAGGCAAGCT

GGGCAAGGCGACGTTCCTGGAAGGCATTATCACCTCCCTGCCGACG

CTGGGTGCAGGCCAGTCAGCCTTTAAAATTAATTTCGAATGGGATG

ACGGCTCTGGTATTCCGGGCGCCTTCTACATCAAGAACTTCATGCA

GACCGAATTTTTCCTGGTCAGCCTGACGCTGGAAGATATCCCGAAT

CATGGCTCGATTCACTTTGTGTGCAACAGCTGGATCTACAATGCGA

AACTGTTCAAGTCCGATCGCATTTTCTTTGCCAATCAGACCTATCT

GCCGTCAGAAACGCCGGCACCGCTGGTTAAATACCGTGAAGAAGAA

CTGCACAACCTGCGTGGTGACGGTACCGGTGAACGTAAAGAATGGG

AACGCATCTACGATTACGACGTTTACAACGATCTGGGTGATCCGGA

CAAAGGCGAAAACCATGCGCGTCCGGTCCTGGGCGGTAATGACACC

TTTCCGTACCCGCGTCGCGGTCGTACCGGTCGTAAACCGACGCGTA

AGGATCCGAACAGCGAATCTCGCAGTAATGATGTGTATCTGCCGCG

TGACGAAGCCTTTGGTCACCTGAAAAGCTCTGATTTCCTGACGTAC

GGCCTGAAGTCCGTTTCACAGAACGTCCTGCCGCTGCTGCAAAGCG

CATTTGATCTGAATTTCACCCCGCGCGAATTTGATTCGTTCGACGA

AGTTCATGGTCTGTATAGCGGCGGTATTAAGCTGCCGACCGACATT

ATCTCTAAAATCAGTCCGCTGCCGGTGCTGAAGGAAATTTTTCGCA

CGGATGGCGAACAGGCTCTGAAGTTCCCGCCGCCGAAAGTCATCCA

AGTGTCGAAAAGCGCGTGGATGACCGATGAAGAATTTGCACGTGAA

ATGCTGGCTGGTGTTAACCCGAATCTGATTCGCTGTCTGAAGGATT

TCCCGCCGCGTTCCAAACTGGATTCACAGGTGTATGGTGACCACAC

CAGTCAAATCACGAAAGAACATCTGGAACCGAACCTGGAAGGCCTG

ACCGTTGATGAAGCTATTCAGAATAAACGTCTGTTTCTGCTGGATC

ATCACGACCCGATCATGCCGTATCTGCGTCGCATTAATGCGACCTC

GACGAAAGCGTACGCCACCCGCACGATCCTGTTCCTGAAGAACGAT

-continued

GGTACCCTGCGTCCGCTGGCCATTGAACTGAGCCTGCCGCATCCGC

AGGGTGACCAATCGGGTGCGTTTAGCCAGGTTTTCCTGCCGGCCGA

TGAAGGCGTCGAAAGTTCCATCTGGCTGCTGGCAAAAGCTTATGTG

GTTGTCAACGATTCTTGCTACCATCAGCTGGTGTCTCACTGGCTGA

ATACCCATGCAGTGGTTGAACCGTTTATTATCGCTACGAACCGCCA

CCTGTCTGTCGTGCATCCGATCTATAAACTGCTGCATCCGCACTAC

CGCGACACCATGAACATTAATGGTCTGGCGCGTCTGAGTCTGGTCA

ACGATGGCGGTGTGATTGAACAGACGTTTCTGTGGGGCCGTTATTC

TGTTGAAATGAGTGCCGTTGTCTACAAAGATTGGGTCTTCACCGAC

CAAGCACTGCCGGCAGACCTGATCAAGCGTGGTATGGCAATTGAAG

ATCCGTCCTGTCCGCACGGCATCCGTCTGGTGATTGAAGATTATCC

GTACACCGTTGACGGTCTGGAAATCTGGGATGCAATTAAAACGTGG

GTGCATGAATACGTTTTTCTGTACTACAAGTCTGATGACACCCTGC

GCGAAGACCCGGAACTGCAGGCGTGCTGGAAAGAACTGGTGGAAGT

TGGTCACGGCGATAAAAAGAACGAACCGTGGTGGCCGAAAATGCAA

ACCCGTGAAGAACTGGTTGAAGCGTGTGCCATTATCATTTGGACGG

CAAGCGCTCTGCATGCGGCCGTGAACTTTGGCCAGTATCCGTACGG

CGGTCTGATTCTGAATCGCCCGACCCTGTCTCGTCGCTTCATGCCG

GAAAAAGGCAGTGCTGAATATGAAGAACTGCGTAAAAATCCGCAGA

AGGCGTACCTGAAAACCATCACGCCGAAATTTCAAACCCTGATTGA

CCTGAGCGTGATCGAAATTCTGTCCCGCCATGCGTCAGATGAAGTT

TATCTGGGTGAACGTGACAACCCGAATTGGACCTCCGATACGCGTG

CACTGGAAGCTTTTAAGCGCTTCGGCAACAAACTGGCCCAGATCGA

AAACAAGCTGTCAGAACGTAACAACGATGAAAAGCTGCGTAATCGC

TGCGGCCCGGTGCAAATGCCGTATACCCTGCTGCTGCCGTCCTCAA

AAGAAGGTCTGACGTTCCGTGGTATCCCGAATAGCATTAGCATCTA

AGAATTC

Minilox optimized encoding sequence (with 5'NdeI and 3'XhoI restriction sites and 3'stop codon for cloning into pJexpress purple 424 vector from DNA2.0 Inc.)

(SEQ ID NO 6)

CATATGTCTACGCCGATTGAATTTCACTCCTTCCAGGACGTTCAT

GATCTGTATGAAGGCGGTATCAAACTGCCGCGTGACGTCATTTCA

ACCATTATCCCGCTGCCGGTGATCAAAGAACTGTACCGCACGGAT

GGTCAGCACATTCTGAAATTTCCGCAACCGCATGTGGTTCAGGTT

TCACAATCGGCGTGGATGACCGATGAAGAATTCGCGCGTGAAATG

ATCGCCGGCGTTAACCCGTGCGTCATTCGCGGTCGGAAGAATTT

CCGCCGAAAAGCAATCTGGACCCGGCAATCTATGGCGATCAGAGT

TCCAAAATTACCGCTGACTCTCTGGACCTGGATGGCTACACGATG

GATGAAGCCCTGGGTAGTCGTCGCCTGTTTATGCTGGACTATCAC

GATATCTTCATGCCGTACGTGCGTCAGATTAACCAACTGAATTCT

GCAAAAACCTATGCTACCCGTACGATCCTGTTTCTGCGCGAAGAC

```
GGCACGCTGAAACCGGTTGCAATTGAACTGAGCCTGCCGCATTCT
GCTGGTGATCTGAGTGCCGCGGTGTCCCAGGTTGTGCTGCCGGCA
AAAGAAGGCGTTGAAAGTACCATCTGGCTGCTGGCGAAAGCCTAT
GTTATTGTCAACGATTCATGTTACCATCAACTGATGTCGCACTGG
CTGAATACCCATGCAGCTATGGAACCGTTTGTTATCGCAACGCAT
CGCCACCTGTCTGTCCTGCACCCGATTTATAAACTGCTGACCCCG
CATTACCGTAACAATATGAACATCAATGCACTGGCTCGCCAGAGT
CTGATTAACGCGAATGGTATTATCGAAACCACGTTCCTGCCGTCA
AAATATTCGGTGGAAATGTCATCGGCCGTTTACAAAAACTGGGTC
TTTACCGACCAGGCACTGCCGGCTGATCTGATCAAACGTGGCGTCG
CGATTAAAGATCCGAGCACCCCGCATGGTGTGCGTCTGCTGATTGA
AGACTATCCGTACGCGGCCGATGGCCTGGAAATCTGGGCAGCTATT
AAAACCTGGGTGCAGGAATATGTTCCGCTGTATTACGCACGCGATG
ACGATGTGAAAAATGACTCCGAACTGCAACACTGGTGGAAAGAAGC
TGTTGAAAAAGGTCATGGCGACCTGAAAGATAAACCGTGGTGGCCG
AAACTGCAGACCCTGGAAGATCTGGTGGAAGTTTGTCTGATTATCA
TTTGGATTGCCAGCGCACTGCATGCCGCGGTGAACTTTGGTCAATA
TCCGTACGGCGGTCTGATTATGAATCGTCCGACCGCAAGCCGTCGC
CTGCTGCCGGAAAAAGGCACGCCGGAATACGAAGAAATGATCAACA
ACCATGAAAAAGCGTACCTGCGCACCATCACGAGCAAACTGCCGAC
CCTGATTAGCCTGTCTGTTATCGAAATTCTGTCAACGCACGCGTCG
GATGAAGTCTATCTGGGTCAGCGTGACAACCCGCATTGGACCAGTG
ATTCCAAAGCGCTGCAGGCCTTCCAAAAATTCGGCAACAAACTGAA
AGAAATCGAAGAAAAACTGGTCCGTCGCAACAATGATCCGAGCCTGC
AGGGTAACCGTCTGGGTCCGGTGCAACTGCCGTATACCCTGCTGTAT
CCGTCCAGTGAAGAAGGTCTGACGTTTCGTGGTATTCCGAACTCCAT
TTCCATCTGACTCGAG
```

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A method of producing lipoxygenase enzyme comprising:
   providing a nucleic acid expression construct within a host microorganism that is generally recognized as safe for the production of food enzymes, wherein the nucleic acid construct encodes a plant lipoxygenase enzyme;
   providing one or more chaperone plasmids within the host microorganism; and
   inducing expression of the plant a lipoxygenase enzyme encoded by the nucleic acid expression construct, wherein the amount of soluble plant lipoxygenase enzyme expressed is 30% or greater relative to the total soluble protein expressed by the host microorganism.

2. The method of claim 1, further comprising purifying the expressed plant lipoxygenase enzyme and collecting purified plant lipoxygenase enzyme.

3. The method of claim 2, wherein purification comprises contacting the expressed plant lipoxygenase enzyme to immobilized-metal affinity chromatography media.

4. The method of claim 1, wherein the nucleic acid expression construct encodes the amino acid sequence of SEQ ID NO: 1, SEQ ID NO: 2, or SEQ ID NO: 3.

5. The method of claim 1, wherein the nucleic acid expression construct encodes the amino acid sequence of SEQ ID NO: 4, SEQ ID NO: 5, or SEQ ID NO: 6.

6. The method of claim 1, wherein the host microorganism is a bacterial cell containing one or more protease deficiencies.

7. The method of claim 6, wherein the bacterial cell is a strain of *Lactoccocus*, K12 cells, *Bacillus* cells, *E. coli* cells or yeast cells.

8. The method of claim 1, wherein the one or more chaperone plasmids are simultaneously co-expressed with the plant lipoxygenase enzyme.

9. The method of claim 1, wherein inducing comprises maintaining the host microorganism at from 10-37° C. for a period of time.

10. The method of claim 9, wherein inducing comprises maintaining the host microorganism at from 25-35° C. for a period of time.

11. The method of claim 9, wherein inducing comprises maintaining the host microorganism at from 10-25° C. for a period of time.

12. The method of claim 9, wherein inducing comprises maintaining the host microorganism at from 20-25° C. for a period of time.

13. The method of claim 9, wherein the period of time is from 1 hour to 2 days.

14. The method of claim 1, wherein the expressed plant lipoxygenase enzyme does not contain a histidine tag.

15. The method of claim 1, wherein the amount of soluble plant lipoxygenase enzyme expressed is 5 fold greater or more than the amount of soluble plant lipoxygenase enzyme expressed from the host microorganism that are not protease deficient or expressed from the host microorganism without an expression chaperone.

16. The method of claim 1, wherein the amount of soluble plant lipoxygenase enzyme expressed is 10 fold greater or more than the amount of soluble plant lipoxygenase enzyme expressed from the host microorganism that are not protease deficient or expressed from the host microorganism without an expression chaperone.

17. The method of claim 1, wherein the amount of soluble plant lipoxygenase enzyme expressed is 100 fold greater or more than the amount of soluble plant lipoxygenase enzyme expressed from the host microorganism that are not protease deficient or expressed from the host microorganism without an expression chaperone.

18. A method of producing lipoxygenase enzyme comprising:
    providing a nucleic acid expression construct within a host microorganism, wherein the nucleic acid expression construct encodes a plant lipoxygenase enzyme and the host microorganism is generally recognized as safe for the production of food enzymes;
    providing one or more chaperone plasmids within the host microorganism wherein the one or more chaperone plasmids are simultaneously co-expressed with the a plant lipoxygenase enzyme;
    inducing expression of the plant lipoxygenase enzyme encoded by the nucleic acid expression construct;
    purifying the expressed plant lipoxygenase enzyme by contacting the expressed plant lipoxygenase enzyme to immobilized-metal affinity chromatography media, wherein the amount of soluble plant lipoxygenase enzyme expressed relative to the total soluble protein expressed in the host microorganism is 30% or greater; and
    collecting purified plant lipoxygenase enzyme.

19. The method of claim 18, wherein the expressed plant lipoxygenase enzyme does not contain a histidine tag.

20. A method of producing a plant lipoxygenase enzyme comprising:
    providing a nucleic acid expression construct within a host microorganism, wherein the construct encodes the plant lipoxygenase enzyme and the host microorganism is generally recognized as safe for the production of food enzymes;
    providing one or more chaperone plasmids within the host microorganism wherein the one or more chaperone plasmids are simultaneously co-expressed with the plant lipoxygenase enzyme;
    inducing expression of the plant lipoxygenase enzyme, which produces 30% or greater amount of soluble plant lipoxygenase enzyme relative to total soluble protein in the host microorganism; and
    collecting the plant lipoxygenase enzyme.

21. The method of claim 20, wherein collecting the plant lipoxygenase enzyme comprises contacting the plant lipoxygenase enzyme to immobilized-metal affinity chromatography media.

22. The method of claim 20, wherein the amount of plant lipoxygenase enzyme collected is 5 fold greater or more than the amount of plant lipoxygenase enzyme collected from the host microorganism that are not protease deficient or from the host microorganism without an expression chaperone.

23. The method of claim 20, wherein the amount of plant lipoxygenase enzyme collected is 10 fold greater or more than the amount of plant lipoxygenase enzyme collected from the host microorganism that are not protease deficient or from the host microorganism without an expression chaperone.

24. The method of claim 20, wherein the amount of plant lipoxygenase enzyme collected is 100 fold greater or more than the amount of plant lipoxygenase enzyme collected from the host microorganism that are not protease deficient or from the host microorganism without an expression chaperone.

* * * * *

SEQUENCE LISTING

```
<160> NUMBER OF SEQ ID NOS: 7

<210> SEQ ID NO 1
<211> LENGTH: 839
<212> TYPE: PRT
<213> ORGANISM: Glycine max

<400> SEQUENCE: 1

Met Phe Ser Ala Gly His Lys Ile Lys Gly Thr Val Val Leu Met Pro
1               5                   10                  15

Lys Asn Glu Leu Glu Val Asn Pro Asp Gly Ser Ala Val Asp Asn Leu
            20                  25                  30

Asn Ala Phe Leu Gly Arg Ser Val Ser Leu Gln Leu Ile Ser Ala Thr
        35                  40                  45

Lys Ala Asp Ala His Gly Lys Gly Lys Val Gly Lys Asp Thr Phe Leu
    50                  55                  60

Glu Gly Ile Asn Thr Ser Leu Pro Thr Leu Gly Ala Gly Glu Ser Ala
65                  70                  75                  80

Phe Asn Ile His Phe Glu Trp Asp Gly Ser Met Gly Ile Pro Gly Ala
                85                  90                  95

Phe Tyr Ile Lys Asn Tyr Met Gln Val Glu Phe Phe Leu Lys Ser Leu
            100                 105                 110

Thr Leu Glu Ala Ile Ser Asn Gln Gly Thr Ile Arg Phe Val Cys Asn
        115                 120                 125

Ser Trp Val Tyr Asn Thr Lys Leu Tyr Lys Ser Val Arg Ile Phe Phe
    130                 135                 140

Ala Asn His Thr Tyr Val Pro Ser Glu Thr Pro Ala Pro Leu Val Ser
145                 150                 155                 160

Tyr Arg Glu Glu Leu Lys Ser Leu Arg Gly Asn Gly Thr Gly Glu
```

```
                    165                 170                 175
Arg Lys Glu Tyr Asp Arg Ile Tyr Asp Tyr Asp Val Tyr Asn Asp Leu
                180                 185                 190
Gly Asn Pro Asp Lys Ser Glu Lys Leu Ala Arg Pro Val Leu Gly Gly
                195                 200                 205
Ser Ser Thr Phe Pro Tyr Pro Arg Arg Gly Arg Thr Gly Arg Gly Pro
            210                 215                 220
Thr Val Thr Asp Pro Asn Thr Glu Lys Gln Gly Glu Val Phe Tyr Val
225                 230                 235                 240
Pro Arg Asp Glu Asn Leu Gly His Leu Ser Lys Asp Ala Leu Glu
                    245                 250                 255
Ile Gly Thr Lys Ser Leu Ser Gln Ile Val Gln Pro Ala Phe Glu Ser
                260                 265                 270
Ala Phe Asp Leu Lys Ser Thr Pro Ile Glu Phe His Ser Phe Gln Asp
            275                 280                 285
Val His Asp Leu Tyr Glu Gly Gly Ile Lys Leu Pro Arg Asp Val Ile
        290                 295                 300
Ser Thr Ile Ile Pro Leu Pro Val Ile Lys Glu Leu Tyr Arg Thr Asp
305                 310                 315                 320
Gly Gln His Ile Leu Lys Phe Pro Gln Pro His Val Val Gln Val Ser
                    325                 330                 335
Gln Ser Ala Trp Met Thr Asp Glu Glu Phe Ala Arg Glu Met Ile Ala
                340                 345                 350
Gly Val Asn Pro Cys Val Ile Arg Gly Leu Glu Glu Phe Pro Pro Lys
            355                 360                 365
Ser Asn Leu Asp Pro Ala Ile Tyr Gly Asp Gln Ser Ser Lys Ile Thr
        370                 375                 380
Ala Asp Ser Leu Asp Leu Asp Gly Tyr Thr Met Asp Glu Ala Leu Gly
385                 390                 395                 400
Ser Arg Arg Leu Phe Met Leu Asp Tyr His Asp Ile Phe Met Pro Tyr
                    405                 410                 415
Val Arg Gln Ile Asn Gln Leu Asn Ser Ala Lys Thr Tyr Ala Thr Arg
                420                 425                 430
Thr Ile Leu Phe Leu Arg Glu Asp Gly Thr Leu Lys Pro Val Ala Ile
            435                 440                 445
Glu Leu Ser Leu Pro His Ser Ala Gly Asp Leu Ser Ala Ala Val Ser
        450                 455                 460
Gln Val Val Leu Pro Ala Lys Glu Gly Val Glu Ser Thr Ile Trp Leu
465                 470                 475                 480
Leu Ala Lys Ala Tyr Val Ile Val Asn Asp Ser Cys Tyr His Gln Leu
                    485                 490                 495
Met Ser His Trp Leu Asn Thr His Ala Ala Met Glu Pro Phe Val Ile
                500                 505                 510
Ala Thr His Arg His Leu Ser Val Leu His Pro Ile Tyr Lys Leu Leu
            515                 520                 525
Thr Pro His Tyr Arg Asn Asn Met Asn Ile Asn Ala Leu Ala Arg Gln
        530                 535                 540
Ser Leu Ile Asn Ala Asn Gly Ile Ile Glu Thr Thr Phe Leu Pro Ser
545                 550                 555                 560
Lys Tyr Ser Val Glu Met Ser Ser Ala Val Tyr Lys Asn Trp Val Phe
                    565                 570                 575
Thr Asp Gln Ala Leu Pro Ala Asp Leu Ile Lys Arg Gly Val Ala Ile
                580                 585                 590
```

```
Lys Asp Pro Ser Thr Pro His Gly Val Arg Leu Leu Ile Glu Asp Tyr
        595                 600                 605

Pro Tyr Ala Ala Asp Gly Leu Glu Ile Trp Ala Ala Ile Lys Thr Trp
    610                 615                 620

Val Gln Glu Tyr Val Pro Leu Tyr Tyr Ala Arg Asp Asp Val Lys
625                 630                 635                 640

Asn Asp Ser Glu Leu Gln His Trp Trp Lys Glu Ala Val Glu Lys Gly
                645                 650                 655

His Gly Asp Leu Lys Asp Lys Pro Trp Trp Pro Lys Leu Gln Thr Leu
            660                 665                 670

Glu Asp Leu Val Glu Val Cys Leu Ile Ile Ile Trp Ile Ala Ser Ala
        675                 680                 685

Leu His Ala Ala Val Asn Phe Gly Gln Tyr Pro Tyr Gly Gly Leu Ile
    690                 695                 700

Met Asn Arg Pro Thr Ala Ser Arg Arg Leu Leu Pro Glu Lys Gly Thr
705                 710                 715                 720

Pro Glu Tyr Glu Glu Met Ile Asn Asn His Glu Lys Ala Tyr Leu Arg
                725                 730                 735

Thr Ile Thr Ser Lys Leu Pro Thr Leu Ile Ser Leu Ser Val Ile Glu
            740                 745                 750

Ile Leu Ser Thr His Ala Ser Asp Glu Val Tyr Leu Gly Gln Arg Asp
        755                 760                 765

Asn Pro His Trp Thr Ser Asp Ser Lys Ala Leu Gln Ala Phe Gln Lys
    770                 775                 780

Phe Gly Asn Lys Leu Lys Glu Ile Glu Glu Lys Leu Val Arg Arg Asn
785                 790                 795                 800

Asn Asp Pro Ser Leu Gln Gly Asn Arg Leu Gly Pro Val Gln Leu Pro
                805                 810                 815

Tyr Thr Leu Leu Tyr Pro Ser Ser Glu Glu Gly Leu Thr Phe Arg Gly
            820                 825                 830

Ile Pro Asn Ser Ile Ser Ile
        835

<210> SEQ ID NO 2
<211> LENGTH: 857
<212> TYPE: PRT
<213> ORGANISM: Glycine max

<400> SEQUENCE: 2

Met Leu Gly Gly Leu Leu His Arg Gly His Lys Ile Lys Gly Thr Val
1               5                   10                  15

Val Leu Met Arg Lys Asn Val Leu Asp Val Asn Ser Val Thr Ser Val
            20                  25                  30

Gly Gly Ile Ile Gly Gln Gly Leu Asp Leu Val Gly Ser Thr Leu Asp
        35                  40                  45

Thr Leu Thr Ala Phe Leu Gly Arg Ser Val Ser Leu Gln Leu Ile Ser
    50                  55                  60

Ala Thr Lys Ala Asp Ala Asn Gly Lys Gly Lys Leu Gly Lys Ala Thr
65                  70                  75                  80

Phe Leu Glu Gly Ile Ile Thr Ser Leu Pro Thr Leu Gly Ala Gly Gln
                85                  90                  95

Ser Ala Phe Lys Ile Asn Phe Glu Trp Asp Asp Gly Ser Gly Ile Pro
            100                 105                 110

Gly Ala Phe Tyr Ile Lys Asn Phe Met Gln Thr Glu Phe Phe Leu Val
```

-continued

```
            115                 120                 125
Ser Leu Thr Leu Glu Asp Ile Pro Asn His Gly Ser Ile His Phe Val
        130                 135                 140
Cys Asn Ser Trp Ile Tyr Asn Ala Lys Leu Phe Lys Ser Asp Arg Ile
145                 150                 155                 160
Phe Phe Ala Asn Gln Thr Tyr Leu Pro Ser Glu Thr Pro Ala Pro Leu
                165                 170                 175
Val Lys Tyr Arg Glu Glu Leu His Asn Leu Arg Gly Asp Gly Thr
            180                 185                 190
Gly Glu Arg Lys Glu Trp Glu Arg Ile Tyr Asp Tyr Asp Val Tyr Asn
            195                 200                 205
Asp Leu Gly Asp Pro Asp Lys Gly Glu Asn His Ala Arg Pro Val Leu
        210                 215                 220
Gly Gly Asn Asp Thr Phe Pro Tyr Pro Arg Arg Gly Arg Thr Gly Arg
225                 230                 235                 240
Lys Pro Thr Arg Lys Asp Pro Asn Ser Glu Ser Arg Ser Asn Asp Val
                245                 250                 255
Tyr Leu Pro Arg Asp Glu Ala Phe Gly His Leu Lys Ser Ser Asp Phe
            260                 265                 270
Leu Thr Tyr Gly Leu Lys Ser Val Ser Gln Asn Val Leu Pro Leu Leu
            275                 280                 285
Gln Ser Ala Phe Asp Leu Asn Phe Thr Pro Arg Glu Phe Asp Ser Phe
        290                 295                 300
Asp Glu Val His Gly Leu Tyr Ser Gly Gly Ile Lys Leu Pro Thr Asp
305                 310                 315                 320
Ile Ile Ser Lys Ile Ser Pro Leu Pro Val Leu Lys Glu Ile Phe Arg
                325                 330                 335
Thr Asp Gly Glu Gln Ala Leu Lys Phe Pro Pro Lys Val Ile Gln
            340                 345                 350
Val Ser Lys Ser Ala Trp Met Thr Asp Glu Glu Phe Ala Arg Glu Met
            355                 360                 365
Leu Ala Gly Val Asn Pro Asn Leu Ile Arg Cys Leu Lys Asp Phe Pro
        370                 375                 380
Pro Arg Ser Lys Leu Asp Ser Gln Val Tyr Gly Asp His Thr Ser Gln
385                 390                 395                 400
Ile Thr Lys Glu His Leu Glu Pro Asn Leu Glu Gly Leu Thr Val Asp
                405                 410                 415
Glu Ala Ile Gln Asn Lys Arg Leu Phe Leu Leu Asp His His Asp Pro
            420                 425                 430
Ile Met Pro Tyr Leu Arg Arg Ile Asn Ala Thr Ser Thr Lys Ala Tyr
            435                 440                 445
Ala Thr Arg Thr Ile Leu Phe Leu Lys Asn Asp Gly Thr Leu Arg Pro
        450                 455                 460
Leu Ala Ile Glu Leu Ser Leu Pro His Pro Gln Gly Asp Gln Ser Gly
465                 470                 475                 480
Ala Phe Ser Gln Val Phe Leu Pro Ala Asp Glu Gly Val Glu Ser Ser
                485                 490                 495
Ile Trp Leu Leu Ala Lys Ala Tyr Val Val Asn Asp Ser Cys Tyr
            500                 505                 510
His Gln Leu Val Ser His Trp Leu Asn Thr His Ala Val Val Glu Pro
            515                 520                 525
Phe Ile Ile Ala Thr Asn Arg His Leu Ser Val Val His Pro Ile Tyr
        530                 535                 540
```

-continued

Lys Leu Leu His Pro His Tyr Arg Asp Thr Met Asn Ile Asn Gly Leu
545                 550                 555                 560

Ala Arg Leu Ser Leu Val Asn Asp Gly Gly Val Ile Glu Gln Thr Phe
            565                 570                 575

Leu Trp Gly Arg Tyr Ser Val Glu Met Ser Ala Val Val Tyr Lys Asp
        580                 585                 590

Trp Val Phe Thr Asp Gln Ala Leu Pro Ala Asp Leu Ile Lys Arg Gly
    595                 600                 605

Met Ala Ile Glu Asp Pro Ser Cys Pro His Gly Ile Arg Leu Val Ile
610                 615                 620

Glu Asp Tyr Pro Tyr Thr Val Asp Gly Leu Gly Ile Trp Asp Ala Ile
625                 630                 635                 640

Lys Thr Trp Val His Glu Tyr Val Phe Leu Tyr Tyr Lys Ser Asp Asp
                645                 650                 655

Thr Leu Arg Glu Asp Pro Glu Leu Gln Ala Cys Trp Lys Glu Leu Val
            660                 665                 670

Glu Val Gly His Gly Asp Lys Lys Asn Glu Pro Trp Trp Pro Lys Met
        675                 680                 685

Gln Thr Arg Glu Glu Leu Val Glu Ala Cys Ala Ile Ile Ile Trp Thr
    690                 695                 700

Ala Ser Ala Leu His Ala Ala Val Asn Phe Gly Gln Tyr Pro Tyr Gly
705                 710                 715                 720

Gly Leu Ile Leu Asn Arg Pro Thr Leu Ser Arg Arg Phe Met Pro Glu
                725                 730                 735

Lys Gly Ser Ala Glu Tyr Glu Glu Leu Arg Lys Asn Pro Gln Lys Ala
            740                 745                 750

Tyr Leu Lys Thr Ile Thr Pro Lys Phe Gln Thr Leu Ile Asp Leu Ser
        755                 760                 765

Val Ile Glu Ile Leu Ser Arg His Ala Ser Asp Glu Val Tyr Leu Gly
    770                 775                 780

Glu Arg Asp Asn Pro Asn Trp Thr Ser Asp Thr Arg Ala Leu Glu Ala
785                 790                 795                 800

Phe Lys Arg Phe Gly Asn Lys Leu Ala Gln Ile Glu Asn Lys Leu Ser
                805                 810                 815

Glu Arg Asn Asn Asp Glu Lys Leu Arg Asn Arg Cys Gly Pro Val Gln
            820                 825                 830

Met Pro Tyr Thr Leu Leu Leu Pro Ser Ser Lys Glu Gly Leu Thr Phe
        835                 840                 845

Arg Gly Ile Pro Asn Ser Ile Ser Ile
    850                 855

<210> SEQ ID NO 3
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ser Thr Pro Ile Glu Phe His Ser Phe Gln Asp Val His Asp Leu
1               5                   10                  15

Tyr Glu Gly Gly Ile Lys Leu Pro Arg Asp Val Ile Ser Thr Ile Ile
                20                  25                  30

Pro Leu Pro Val Ile Lys Glu Leu Tyr Arg Thr Asp Gly Gln His Ile

```
            35                  40                  45
Leu Lys Phe Pro Gln Pro His Val Val Gln Val Ser Gln Ser Ala Trp
 50                  55                  60

Met Thr Asp Glu Glu Phe Ala Arg Glu Met Ile Ala Gly Val Asn Pro
 65                  70                  75                  80

Cys Val Ile Arg Gly Leu Glu Glu Phe Pro Pro Lys Ser Asn Leu Asp
                     85                  90                  95

Pro Ala Ile Tyr Gly Asp Gln Ser Ser Lys Ile Thr Ala Asp Ser Leu
                    100                 105                 110

Asp Leu Asp Gly Tyr Thr Met Asp Glu Ala Leu Gly Ser Arg Arg Leu
                    115                 120                 125

Phe Met Leu Asp Tyr His Asp Ile Phe Met Pro Tyr Val Arg Gln Ile
                    130                 135                 140

Asn Gln Leu Asn Ser Ala Lys Thr Tyr Ala Thr Arg Thr Ile Leu Phe
145                 150                 155                 160

Leu Arg Glu Asp Gly Thr Leu Lys Pro Val Ala Ile Glu Leu Ser Leu
                    165                 170                 175

Pro His Ser Ala Gly Asp Leu Ser Ala Val Ser Gln Val Val Leu
                    180                 185                 190

Pro Ala Lys Glu Gly Val Glu Ser Thr Ile Trp Leu Leu Ala Lys Ala
                    195                 200                 205

Tyr Val Ile Val Asn Asp Ser Cys Tyr His Gln Leu Met Ser His Trp
210                 215                 220

Leu Asn Thr His Ala Ala Met Glu Pro Phe Val Ile Ala Thr His Arg
225                 230                 235                 240

His Leu Ser Val Leu His Pro Ile Tyr Lys Leu Leu Thr Pro His Tyr
                    245                 250                 255

Arg Asn Asn Met Asn Ile Asn Ala Leu Ala Arg Gln Ser Leu Ile Asn
                    260                 265                 270

Ala Asn Gly Ile Ile Glu Thr Thr Phe Leu Pro Ser Lys Tyr Ser Val
                    275                 280                 285

Glu Met Ser Ser Ala Val Tyr Lys Asn Trp Val Phe Thr Asp Gln Ala
                    290                 295                 300

Leu Pro Ala Asp Leu Ile Lys Arg Gly Val Ala Ile Lys Asp Pro Ser
305                 310                 315                 320

Thr Pro His Gly Val Arg Leu Leu Ile Glu Asp Tyr Pro Tyr Ala Ala
                    325                 330                 335

Asp Gly Leu Glu Ile Trp Ala Ala Ile Lys Thr Trp Val Gln Glu Tyr
                    340                 345                 350

Val Pro Leu Tyr Tyr Ala Arg Asp Asp Val Lys Asn Asp Ser Glu
                    355                 360                 365

Leu Gln His Trp Trp Lys Glu Ala Val Glu Lys Gly His Gly Asp Leu
                    370                 375                 380

Lys Asp Lys Pro Trp Trp Pro Lys Leu Gln Thr Leu Glu Asp Leu Val
385                 390                 395                 400

Glu Val Cys Leu Ile Ile Ile Trp Ile Ala Ser Ala Leu His Ala Ala
                    405                 410                 415

Val Asn Phe Gly Gln Tyr Pro Tyr Gly Gly Leu Ile Met Asn Arg Pro
                    420                 425                 430

Thr Ala Ser Arg Arg Leu Leu Pro Glu Lys Gly Thr Pro Glu Tyr Glu
                    435                 440                 445

Glu Met Ile Asn Asn His Glu Lys Ala Tyr Leu Arg Thr Ile Thr Ser
450                 455                 460
```

```
Lys Leu Pro Thr Leu Ile Ser Leu Ser Val Ile Glu Ile Leu Ser Thr
465                 470                 475                 480

His Ala Ser Asp Glu Val Tyr Leu Gly Gln Arg Asp Asn Pro His Trp
            485                 490                 495

Thr Ser Asp Ser Lys Ala Leu Gln Ala Phe Gln Lys Phe Gly Asn Lys
        500                 505                 510

Leu Lys Glu Ile Glu Glu Lys Leu Val Arg Arg Asn Asn Asp Pro Ser
    515                 520                 525

Leu Gln Gly Asn Arg Leu Gly Pro Val Gln Leu Pro Tyr Thr Leu Leu
    530                 535                 540

Tyr Pro Ser Ser Glu Glu Gly Leu Thr Phe Arg Gly Ile Pro Asn Ser
545                 550                 555                 560

Ile Ser Ile

<210> SEQ ID NO 4
<211> LENGTH: 2532
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cccgggatgt ttagtgctgg tcacaaaatc aaaggtaccg tggtcctgat gccgaaaaat      60
gaactggaag tcaacccgga tggtagcgcc gttgataacc tgaatgcgtt cctgggtcgt     120
agcgtgtctc tgcagctgat ttccgccacc aaagcagacg ctcacggcaa gggtaaagtt     180
ggcaaagata cgtttctgga aggtattaat acctccctgc cgaccctggg tgccggtgaa     240
tcagctttca acatccattt cgaatgggat ggttcaatgg cattccgggc gccttctac     300 atcaaaaact acatgcaggt ggaatttttc ctgaaaagtc tgaccctgga agcaatctcc     360
aatcagggta cgattcgttt tgtctgcaac tcgtgggtgt ataataccaa actgtacaaa     420
agcgttcgca tcttttttcgc gaaccacacc tatgttccga gcgaaaccc ggcaccgctg     480 gtttcttacc gtgaagaaga actgaaaagt ctgcgcggca atggtaccgg cgaacgtaaa     540
gaatatgatc gcatttatga ctacgatgtt tacaacgacc tgggcaatcc ggataaaagc     600
gaaaaactgg cccgtccggt cctgggcggt agctctacct tcccgtatcc gcgtcgcggt     660
cgtaccggtc gtggtccgac cgtgaccgat ccgaacaccg aaaaacaggg cgaagtcttt     720
tatgtgccgc gcgacgaaaa tctgggccat ctgaaatcta agatgccct ggaaatcggt     780 accaaaagtc tgtcccagat tgtgcaaccg gcgtttgaaa gcgccttcga tctgaaatct     840
acgccgattg aatttcactc cttccaggac gttcatgatc tgtatgaagg cggtatcaaa     900
ctgccgcgtg acgtcatttc aaccattatc ccgctgccgg tgatcaaaga actgtaccgc     960
acggatggtc agcacattct gaaatttccg caaccgcatg tggttcaggt ttcacaatcg    1020
gcgtggatga ccgatgaaga attcgcgcgt gaaatgatcg ccggcgttaa cccgtgcgtc    1080
attcgcggtc tggaagaatt tccgccgaaa agcaatctgg acccggcaat ctatggcgat    1140
cagagttcca aaattaccgc tgactctctg gacctggatg gctacacgat ggatgaagcc    1200
ctgggtagtc gtcgcctgtt tatgctggac tatcacgata tcttcatgcc gtacgtgcgt    1260
cagattaacc aactgaattc tgcaaaaacc tatgctaccc gtacgatcct gtttctgcgc    1320
gaagacggca cgctgaaacc ggttgcaatt gaactgagcc tgccgcattc tgctggtgat    1380
ctgagtgccg cggtgtccca ggttgtgctg ccggcaaaag aaggcgttga agtaccatc     1440
```

```
tggctgctgg cgaaagccta tgttattgtc aacgattcat gttaccatca actgatgtcg   1500
cactggctga ataccatgc agctatggaa ccgtttgtta tcgcaacgca tcgccacctg   1560
tctgtcctgc acccgattta taaactgctg accccgcatt accgtaacaa tatgaacatc   1620
aatgcactgg ctcgccagag tctgattaac gcgaatggta ttatcgaaac cacgttcctg   1680
ccgtcaaaat attcggtgga atgtcatcg gccgtttaca aaaactgggt ctttaccgac   1740
caggcactgc cggctgatct gatcaaacgt ggcgtcgcga ttaaagatcc gagcaccccg   1800
catggtgtgc gtctgctgat tgaagactat ccgtacgcgg ccgatggcct ggaaatctgg   1860
gcagctatta aaacctgggt gcaggaatat gttccgctgt attacgcacg cgatgacgat   1920
gtgaaaaatg actccgaact gcaacactgg tggaagaag ctgttgaaaa aggtcatggc   1980
gacctgaaag ataaaccgtg gtggccgaaa ctgcagaccc tggaagatct ggtggaagtt   2040
tgtctgatta tcatttggat tgccagcgca ctgcatgccg cggtgaactt tggtcaatat   2100
ccgtacggcg gtctgattat gaatcgtccg accgcaagcc gtcgcctgct gccggaaaaa   2160
ggcacgccgg aatacgaaga aatgatcaac aaccatgaaa aagcgtacct gcgcaccatc   2220
acgagcaaac tgccgaccct gattagcctg tctgttatcg aaattctgtc aacgcacgcg   2280
tcggatgaag tctatctggg tcagcgtgac aacccgcatt ggaccagtga ttccaaagcg   2340
ctgcaggcct tccaaaaatt cggcaacaaa ctgaaagaaa tcgaagaaaa actggtccgt   2400
cgcaacaatg atccgagcct gcagggtaac cgtctgggtc cggtgcaact gccgtatacc   2460
ctgctgtatc cgtccagtga agaaggtctg acgtttcgtg gtattccgaa ctccatttcc   2520
atctgactcg ag                                                       2532
```

<210> SEQ ID NO 5
<211> LENGTH: 2583
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
catatgctgg gcggcctgct gcaccgtggt cataaaatca agggcaccgt ggtcctgatg   60
cgtaagaacg tcctggatgt gaatagcgtg acctcggtcg gcggtattat cggccagggt   120
ctggacctgg tgggtagcac gctggatacc ctgacggcct ttctgggccg ctcagtgtcg   180
ctgcaactga tcagcgcaac caaagcagat gctaacggca aaggcaagct gggcaaggcg   240
acgttcctgg aaggcattat cacctccctg ccgacgctgg gtgcaggcca gtcagccttt   300
aaaattaatt tcgaatggga tgacggctct ggtattccgg gcgccttcta catcaagaac   360
ttcatgcaga ccgaattttt cctggtcagc ctgacgctgg aagatatccc gaatcatggc   420
tcgattcact ttgtgtgcaa cagctggatc tacaatgcga actgttcaa gtccgatcgc   480 atttttcttg ccaatcagac ctatctgccg tcagaaacgc cggcaccgct ggttaaatac   540
cgtgaagaag aactgcacaa cctgcgtggt gacggtaccg tgaacgtaa agaatgggaa   600 cgcatctacg attcgacgt ttacaacgat ctgggtgatc cggacaaagg cgaaaaccat   660
gcgcgtccgg tcctgggcgg taatgacacc tttccgtacc cgcgtcgcgg tcgtaccggt   720
cgtaaaccga cgcgtaagga tccgaacagc gaatctcgca gtaatgatgt gtatctgccg   780
cgtgacgaag cctttggtca cctgaaaagc tctgattcc tgacgtacgg cctgaagtcc   840
gtttcacaga acgtcctgcc gctgctgcaa agcgcatttg atctgaattt caccccgcgc   900
```

```
gaatttgatt cgttcgacga agttcatggt ctgtatagcg gcggtattaa gctgccgacc      960
gacattatct ctaaaatcag tccgctgccg gtgctgaagg aaattttcg cacggatggc     1020 gaacaggctc tgaagttccc gccgccgaaa gtcatccaag tgtcgaaaag cgcgtggatg     1080
accgatgaag aatttgcacg tgaaatgctg gctggtgtta acccgaatct gattcgctgt     1140
ctgaaggatt tcccgccgcg ttccaaactg gattcacagg tgtatggtga ccacaccagt     1200
caaatcacga agaacatct ggaaccgaac ctggaaggcc tgaccgttga tgaagctatt      1260
cagaataaac gtctgtttct gctggatcat cacgacccga tcatgccgta tctgcgtcgc     1320
attaatgcga cctcgacgaa agcgtacgcc acccgcacga tcctgttcct gaagaacgat     1380
ggtaccctgc gtccgctggc cattgaactg agcctgccgc atccgcaggg tgaccaatcg     1440
ggtgcgttta gccaggtttt cctgccggcc gatgaaggcg tcgaaagttc catctggctg     1500
ctggcaaaag cttatgtggt tgtcaacgat tcttgctacc atcagctggt gtctcactgg     1560
ctgaataccc atgcagtggt tgaaccgttt attatcgcta cgaaccgcca cctgtctgtc     1620
gtgcatccga tctataaact gctgcatccg cactaccgcg acaccatgaa cattaatggt     1680
ctggcgcgtc tgagtctggt caacgatggc ggtgtgattg aacagacgtt tctgtggggc     1740
cgttattctg ttgaaatgag tgccgttgtc tacaaagatt gggtcttcac cgaccaagca     1800
ctgccggcag acctgatcaa gcgtggtatg gcaattgaag atccgtcctg tccgcacggc     1860
atccgtctgg tgattgaaga ttatccgtac accgttgacg gtctggaaat ctgggatgca     1920
attaaaacgt gggtgcatga atacgttttt ctgtactaca agtctgatga cacctgcgc     1980 gaagacccgg aactgcaggc gtgctggaaa gaactggtgg aagttggtca cggcgataaa     2040
aagaacgaac cgtggtggcc gaaaatgcaa acccgtgaag aactggttga agcgtgtgcc     2100
attatcattt ggacggcaag cgctctgcat gcggccgtga actttggcca gtatccgtac     2160
ggcggtctga ttctgaatcg cccgacctg tctcgtcgct tcatgccgga aaaaggcagt      2220
gctgaatatg aagaactgcg taaaaatccg cagaaggcgt acctgaaaac catcacgccg     2280
aaatttcaaa ccctgattga cctgagcgtg atcgaaattc tgtcccgcca tgcgtcagat     2340
gaagtttatc tgggtgaacg tgacaacccg aattggacct ccgatacgcg tgcactggaa     2400
gcttttaagc gcttcggcaa caaactggcc cagatcgaaa acaagctgtc agaacgtaac     2460
aacgatgaaa agctgcgtaa tcgctgcggc ccggtgcaaa tgccgtatac cctgctgctg     2520
ccgtcctcaa aagaaggtct gacgttccgt ggtatcccga atagcattag catctaagaa     2580
ttc                                                                   2583

<210> SEQ ID NO 6
<211> LENGTH: 1701
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
catatgtcta cgccgattga atttcactcc ttccaggacg ttcatgatct gtatgaaggc       60
ggtatcaaac tgccgcgtga cgtcatttca accattatcc cgctgccggt gatcaaagaa      120
ctgtaccgca cggatggtca gcacattctg aaatttccgc aaccgcatgt ggttcaggtt      180
tcacaatcgg cgtggatgac cgatgaagaa ttcgcgcgtg aaatgatcgc cggcgttaac      240
```

```
ccgtgcgtca ttcgcggtct ggaagaattt ccgccgaaaa gcaatctgga cccggcaatc      300
tatggcgatc agagttccaa aattaccgct gactctctgg acctggatgg ctacacgatg      360
gatgaagccc tgggtagtcg tcgcctgttt atgctggact atcacgatat cttcatgccg      420
tacgtgcgtc agattaacca actgaattct gcaaaaacct atgctacccg tacgatcctg      480
tttctgcgcg aagacggcac gctgaaaccg gttgcaattg aactgagcct gccgcattct      540
gctggtgatc tgagtgccgc ggtgtcccag gttgtgctgc cggcaaaaga aggcgttgaa      600
agtaccatct ggctgctggc gaaagcctat gttattgtca acgattcatg ttaccatcaa      660
ctgatgtcgc actggctgaa tacccatgca gctatgaacc gtttgttat cgcaacgcat       720 cgccacctgt ctgtcctgca cccgatttat aaactgctga ccccgcatta ccgtaacaat      780
atgaacatca atgcactggc tcgccagagt ctgattaacg cgaatggtat tatcgaaacc      840
acgttcctgc cgtcaaaata ttcggtggaa atgtcatcgg ccgtttacaa aaactgggtc      900
tttaccgacc aggcactgcc ggctgatctg atcaaacgtg gcgtcgcgat taaagatccg      960 agcacccgc atggtgtgcg tctgctgatt gaagactatc cgtacgcggc cgatggcctg       1020
gaaatctggg cagctattaa aacctggtg caggaatatg ttccgctgta ttacgcacgc       1080
gatgacgatg tgaaaaatga ctccgaactg caacactggt ggaagaagc tgttgaaaaa       1140 ggtcatggcg acctgaaaga taaaccgtgg tggccgaaac tgcagaccct ggaagatctg      1200
gtggaagttt gtctgattat catttggatt gccagcgcac tgcatgccgc ggtgaacttt      1260
ggtcaatatc cgtacggcgg tctgattatg aatcgtccga ccgcaagccg tcgcctgctg      1320
ccggaaaaag gcacgccgga atacgaagaa atgatcaaca accatgaaaa agcgtacctg      1380
cgcaccatca cgagcaaact gccgacccctg attagcctgt ctgttatcga aattctgtca      1440
acgcacgcgt cggatgaagt ctatctgggt cagcgtgaca acccgcattg gaccagtgat      1500
tccaaagcgc tgcaggcctt ccaaaaattc ggcaacaaac tgaaagaaat cgaagaaaaa      1560
ctggtccgtc gcaacaatga tccgagcctg cagggtaacc gtctgggtcc ggtgcaactg      1620
ccgtataccc tgctgtatcc gtccagtgaa gaaggtctga cgtttcgtgg tattccgaac      1680
tccatttcca tctgactcga g                                                1701
```

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5